United States Patent
Weig (10) Patent No.: US 8,388,586 B2
(45) Date of Patent: Mar. 5, 2013

(54) SEAL FOR AN OSTOMY APPLIANCE

(75) Inventor: Bret Weig, Browns Mills, NJ (US)

(73) Assignee: ConvaTec Technologies, Inc., Las Vegas, NV (US)

( * ) Notice: Subject to any disclaimer, the term of this patent is extended or adjusted under 35 U.S.C. 154(b) by 418 days.

(21) Appl. No.: 12/527,722

(22) PCT Filed: Feb. 21, 2008

(86) PCT No.: PCT/US2008/054518
§ 371 (c)(1),
(2), (4) Date: Aug. 19, 2009

(87) PCT Pub. No.: WO2008/103789
PCT Pub. Date: Aug. 28, 2008

(65) Prior Publication Data
US 2010/0069859 A1 Mar. 18, 2010

Related U.S. Application Data

(60) Provisional application No. 60/891,120, filed on Feb. 22, 2007, provisional application No. 60/891,127, filed on Feb. 22, 2007.

(51) Int. Cl.
*A61F 5/445* (2006.01)
*A61M 25/10* (2006.01)

(52) U.S. Cl. ............... 604/338; 604/101.05; 604/103.08

(58) Field of Classification Search .......... 604/332–345, 604/101.01, 101.05, 103.08, 355, 919
See application file for complete search history.

(56) References Cited

U.S. PATENT DOCUMENTS

| | | | | |
|---|---|---|---|---|
| 2,078,686 A | * | 4/1937 | Rowe | 604/103.02 |
| 2,563,597 A | * | 8/1951 | Friedman | 604/339 |
| 2,610,626 A | * | 9/1952 | Edwards | 604/103.11 |
| 3,100,488 A | * | 8/1963 | Orowan | 604/342 |
| 3,154,077 A | * | 10/1964 | Cannon | 606/192 |
| 3,459,175 A | * | 8/1969 | Miller | 600/431 |
| 3,509,884 A | * | 5/1970 | Bell | 604/101.05 |
| 3,630,206 A | * | 12/1971 | Gingold | 604/103.08 |
| 3,828,782 A | * | 8/1974 | Polin | 604/103.03 |
| 3,915,171 A | * | 10/1975 | Shermeta | 604/101.05 |
| 4,019,515 A | * | 4/1977 | Kornblum et al. | 604/101.05 |
| 4,141,364 A | * | 2/1979 | Schultze | 128/207.15 |
| 4,241,735 A | * | 12/1980 | Chernov | 606/192 |
| 4,344,434 A | * | 8/1982 | Robertson | 604/334 |
| 4,555,242 A | * | 11/1985 | Saudagar | 604/103.08 |
| 4,650,463 A | * | 3/1987 | LeVeen et al. | 604/43 |
| 4,676,228 A | * | 6/1987 | Krasner et al. | 600/116 |
| 4,705,502 A | * | 11/1987 | Patel | 604/544 |

(Continued)

FOREIGN PATENT DOCUMENTS

EP 0168967 1/1986
EP 1346711 9/2003

(Continued)

*Primary Examiner* — Melanie Hand
*Assistant Examiner* — Paula Craig
(74) *Attorney, Agent, or Firm* — Stuart E. Krieger (57) ABSTRACT

An ostomy appliance is disclosed with an inflatable seal for sealing against the stoma. The inflatable seal has a first inflatable chamber portion for fitting inside the stoma to seal against the internal tissue. The inflatable seal also has a second inflatable chamber portion for sealing externally against the stoma and peristomal skin. In one embodiment, a tube extends through the inflatable seal to provide a communication passage for discharge of body waste without removing the inflatable seal. The tube floats with respect to an adhesive mounting member to allow a waist between the first and second inflatable chamber portions to self-locate in the stoma.

21 Claims, 8 Drawing Sheets

U.S. PATENT DOCUMENTS

| | | | | | |
|---|---|---|---|---|---|
| 4,721,508 | A | * | 1/1988 | Burton | 604/338 |
| 4,941,877 | A | * | 7/1990 | Montano, Jr. | 604/103.07 |
| 4,950,223 | A |  | 8/1990 | Silvanov | |
| 5,045,052 | A | * | 9/1991 | Sans | 600/32 |
| 5,147,302 | A | * | 9/1992 | Euteneuer et al. | 604/103 |
| 5,188,623 | A | * | 2/1993 | Kok et al. | 604/328 |
| 5,195,970 | A | * | 3/1993 | Gahara | 604/103.08 |
| 5,342,301 | A | * | 8/1994 | Saab | 604/103.13 |
| 5,366,478 | A | * | 11/1994 | Brinkerhoff et al. | 606/213 |
| 5,395,333 | A | * | 3/1995 | Brill | 604/101.05 |
| 5,397,307 | A | * | 3/1995 | Goodin | 604/103.07 |
| 5,415,634 | A | * | 5/1995 | Glynn et al. | 604/103.08 |
| 5,458,572 | A | * | 10/1995 | Campbell et al. | 604/103.08 |
| 5,545,132 | A | * | 8/1996 | Fagan et al. | 604/103.08 |
| 5,569,216 | A | * | 10/1996 | Kim | 604/277 |
| 5,620,457 | A | * | 4/1997 | Pinchasik et al. | 606/194 |
| 5,634,937 | A | * | 6/1997 | Mollenauer et al. | 606/213 |
| 5,653,701 | A | * | 8/1997 | Millman | 604/345 |
| 5,782,800 | A | * | 7/1998 | Yoon | 604/514 |
| 5,803,921 | A | * | 9/1998 | Bonadio | 606/1 |
| 5,935,115 | A | * | 8/1999 | Espina | 604/277 |
| 6,129,706 | A | * | 10/2000 | Janacek | 604/103.08 |
| 6,249,708 | B1 | * | 6/2001 | Nelson et al. | 607/122 |
| 6,485,476 | B1 |  | 11/2002 | Von Dyke | |
| 6,544,224 | B1 | * | 4/2003 | Steese-Bradley | 604/103.06 |
| 2001/0047188 | A1 | * | 11/2001 | Bonadio et al. | 606/213 |
| 2003/0220621 | A1 |  | 11/2003 | Arkinstall | |
| 2004/0193122 | A1 | * | 9/2004 | Cline et al. | 604/332 |
| 2006/0058576 | A1 |  | 3/2006 | Davies | |
| 2006/0058577 | A1 |  | 3/2006 | Davies | |
| 2006/0079838 | A1 | * | 4/2006 | Walker et al. | 604/104 |
| 2007/0021651 | A1 | * | 1/2007 | Gobel | 600/31 |
| 2007/0123832 | A1 | * | 5/2007 | Cline et al. | 604/335 |
| 2007/0191794 | A1 | * | 8/2007 | Cline et al. | 604/335 |
| 2007/0213661 | A1 | * | 9/2007 | Gobel | 604/96.01 |
| 2008/0262449 | A1 | * | 10/2008 | Shah et al. | 604/339 |
| 2008/0262450 | A1 | * | 10/2008 | Shah et al. | 604/339 |
| 2009/0043151 | A1 | * | 2/2009 | Gobel | 600/31 |
| 2009/0157026 | A1 | * | 6/2009 | Elliott | 604/361 |
| 2010/0022976 | A1 | * | 1/2010 | Weig | 604/355 |
| 2010/0137821 | A1 | * | 6/2010 | Hansen et al. | 604/338 |
| 2010/0174253 | A1 | * | 7/2010 | Cline et al. | 604/328 |
| 2011/0092929 | A1 | * | 4/2011 | Weig | 604/338 |

FOREIGN PATENT DOCUMENTS

| | | |
|---|---|---|
| JP | 10-234854 | 9/1998 |

\* cited by examiner

SEAL FOR AN OSTOMY APPLIANCE

This application is a national stage of PCT/US2008/054518, filed Feb. 21, 2008, and claims priority to U.S. Provisional Patent Application Nos. 60/891,120 filed Feb. 22, 2007, and 60/891,127, filed Feb. 22, 2007.

FIELD OF THE INVENTION

The present invention relates to the field of ostomy appliances for fitting to an ostomate's stoma. One aspect of the invention relates to the formation of a seal around the stoma.

BACKGROUND TO THE INVENTION

Creating a seal around a person's stoma, such that the seal is dependable, comfortable and conducive to body tissue, is important for the function of ostomy appliances. Once this seal has been made, the ostomy appliance may use one or more of a variety of techniques for managing stomal discharge. The term "ostomy" includes colostomy, ileostomy and urostomy. The formation of such a seal remains an area of continuous improvement and development, since the performance and comfort of the seal is fundamental to customer acceptance. One issue is protection of the external peristomal tissue where the normal skin and stoma tissue meet. Peristomal tissue can be extremely sensitive. Irritation can result if the peristomal tissue is exposed to body waste, or to repeated application and removal of adhesive or other sealants.

Some known devices use a single expandable balloon or member inside the stoma to form a seal against the inside wall of the opening, and a fixed stop or surface against the outside of the body. However, such devices have to be designed carefully to avoid the risk of damage to the sensitive internal tissue. In such designs, a relatively high concentration of force may result on the tissue underneath the stoma, especially when the external surface or stop is of limited conformability.

By way of example, U.S. Patent Publication No. 2003/0220621 describes a valved ostomy device including a hollow discharge tube and anchoring means for anchoring the tube in the stoma. The anchoring means comprises an inflatable balloon cuff inserted in the stoma to anchor the tube against the stomal wall, and a screw threaded clamp as an outer stop surface. Although the screw threaded clamp has a conformable pad, the anchoring means bears the entire weight of the ostomy appliance and any collection device attached to it. Thus, the strength of the attachment has to be offset against limitations on the clamping force which can be applied through the peristomal tissue without causing discomfort and tissue damage, and the inflation pressure of the balloon cuff without causing internal tissue damage to the stoma lumen.

EP0168967, EP1346711 and U.S. Pat. No. 4,950,223 describe ostomy ports comprising a single inflatable balloon inserted into the stoma, and an external adhesive wafer for securing the appliance to the skin around the stoma. Such designs are concerned primarily with the formation of a seal inside the stoma lumen. The peristomal tissue is either unprotected or is protected by the adhesive wafer, leaving the possibility that the peristomal tissue may be vulnerable to the conventional problem of irritation and pain resulting from exposure to stool or repeated applications and removals of adhesive.

Inflatable seals are also known from the field of rectal appliances. However, such designs are not generally applicable to ostomy appliances, because the anus is very different physically from a stoma. Nature has engineered the anus to be naturally robust to withstand exposure of tissue to stool, and the pressures associated with containing stool. In contrast, a stoma is an artificial opening formed by surgery, and is much more delicate. Moreover, ostomy appliances often have to carry the long-term weight of a collection pouch, whereas rectal devices normally do not have to support such long-term weight.

SUMMARY OF THE INVENTION

One aspect of the invention provides an inflatable seal for an ostomy appliance. The inflatable seal has one or more of the following features:

(a) a first inflatable chamber portion for sealing against the internal wall of the stoma, and a second inflatable chamber portion for sealing against tissue externally of the stoma. Preferably, the first inflatable chamber portion is insertable into the interior of the bowel behind the stoma mouth and/or into the interior of the stoma below skin level. Additionally or alternatively, the first and second chamber portions are spaced from one another in a direction parallel to an axis of the stoma. In one form, if the two chamber portions communicate with each other, such communication is via an elongate lumen or passage. Preferably, in the inflated condition, the periphery of the second chamber portion extends laterally beyond the periphery of the first chamber portion.

(b) be positioned in the aperture of an adhesive member and includes an inflatable chamber portion and a support, which provides a backbone for the inflatable chamber portion that allows the support to float somewhat with respect to the adhesive member;

(c) an inflatable chamber portion that is located in the aperture of an adhesive member, and is configured to seal externally of the stoma, without substantially occluding the stoma; and/or (d) a tubular member or passage that extends through the external inflatable chamber portion for discharge of body waste allowing the discharge of body waste without removal of the inflatable seal from the stoma.

As used herein, the term "inflatable" means a chamber portion that is configured to be expanded by inflating the chamber with a positive inflation pressure (e.g., a pressure of inflation fluid greater than the external pressure).

Features and advantages of the invention include providing an ostomy seal that is comfortable and effective without creating high concentrations of pressure internally or externally, and which can produce a comfortable peristomal seal.

Although certain features have been highlighted above and in the appended claims, the Applicant may seek protection for any novel feature and/or idea described and/or illustrated herein whether or not emphasis has been placed thereon.

DETAILED DESCRIPTION OF PREFERRED EMBODIMENTS

Referring to FIGS. 1-5 in which an ostomy appliance 20 includes a seal for sealing around a stoma 22. The seal comprises a first inflatable chamber portion 24 for insertion into the stoma 22 for sealing against the internal wall of the stoma lumen 23, and a second inflatable chamber portion 26 for sealing against the external tissue around the stoma 22 and/or against the surrounding peristomal tissue 27. In the first embodiment (FIG. 1), the seal substantially occludes the stoma 22 in order to block discharge of body waste. In the second embodiment (FIG. 2), the seal does not occlude the stoma 22, but provides a seal around the periphery of the stoma 22 for sealing between the ostomy appliance 20 and the stoma 22. The ostomy appliance 20 of the second embodiment permits the discharge of body waste without removal of the seal.

Figure 1:
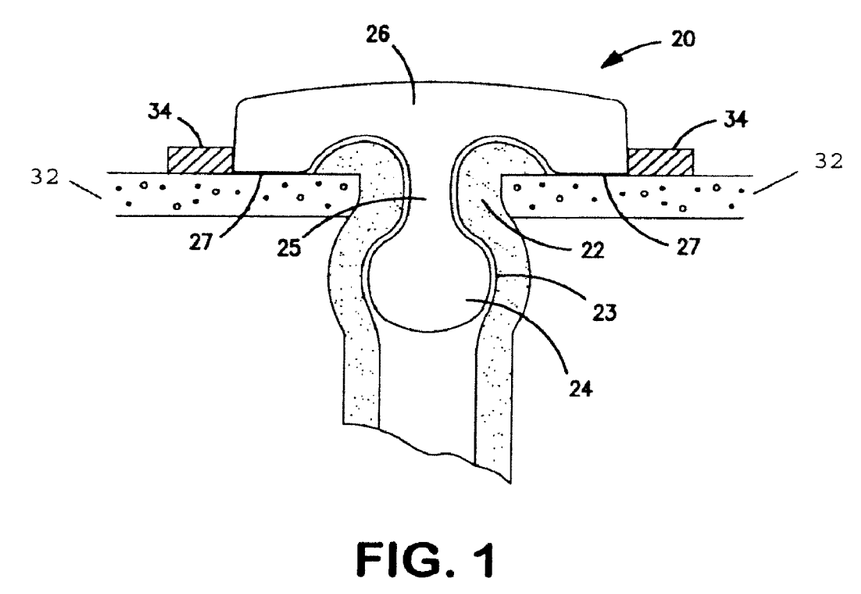
FIG. 1 is a schematic sectional view of a first embodiment of the invention in an inflated condition.
Figure 2:
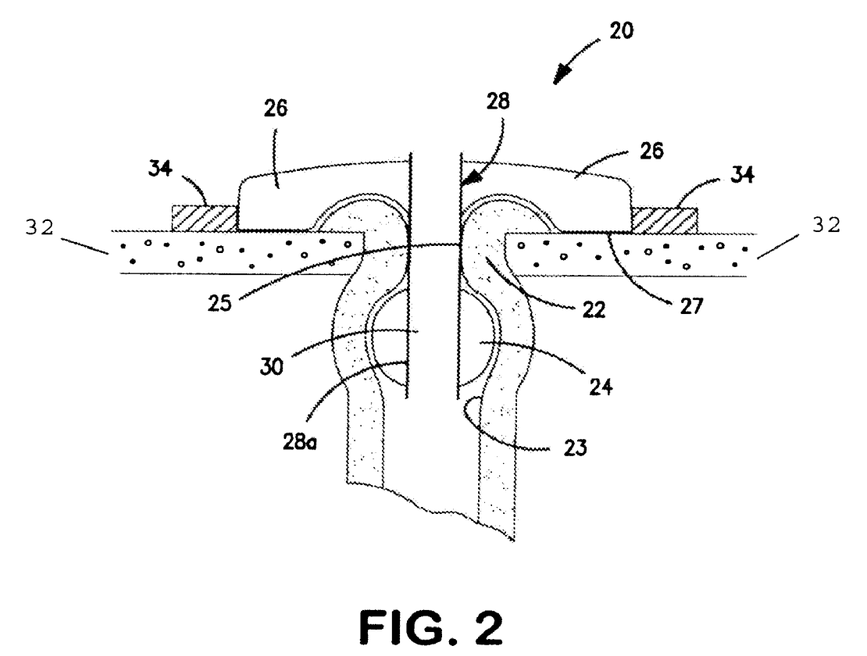
FIG. 2 is a schematic sectional view of a second embodiment of the invention, in an inflated condition.

The use of first and second inflatable chamber portions 24, 26 internally and externally provides one or more of the following advantages:

(a) The first and second inflatable chamber portions 24, 26 provide a more conformable fit both internally and externally of the stoma 22, enabling sealing contact to be maintained at a lower sealing pressure than in some prior designs and the seal contact to be spread over a larger area of body tissue, both internal and external, thereby avoiding concentrated pressure points on the tissue.

(b) The first and second chamber portions 24, 26 can adapt easily to different sizes and shapes of stoma, including stomas with shape irregularities, and recessed stomas, providing a highly versatile seal, both internally and externally.

(c) The second chamber portion 26 can provide non-adhesive, closely fitting protection for the sensitive peristomal tissue, thereby preventing exposure to body waste, and avoiding pain and irritation in the peristomal tissue sometimes associated with purely adhesive seals. If desired, in some applications, the second chamber portion 26 may carry a weak adhesive, or other sealant, to provide secondary seal characteristics.

(d) In addition to providing a seal, the first and second inflatable chamber portions 24, 26 cushion the stoma 22 both internally and externally, resulting in an eminently comfortable fit and providing a degree of protection against external physical knocks or rubbing, which can sometimes be painful on the stoma.

(e) The conformability of the first and second inflatable chamber portions 24, 26 can reduce limitations on the wearer's mobility, and can also reduce the effects of movement on the seal itself by conforming to the body's dynamically moving contours.

A narrow neck or waist 25 is defined between the first and second chamber portions 24, 26. In use, the waist 25 is positioned generally at the stoma 22, such that inflation of the first and second chamber portions 24, 26 sandwiches the stoma 22 on both sides.

The first and second chamber portions 24, 26 may be of approximately the same shape and/or size, or one chamber portion may be larger than the other and/or have a different shape. The first chamber portion 24 has a shape configured for sealing against the internal tissue of the stoma 22 and/or against the stoma lumen 23. For example, the first chamber portion 24 may have a generally rounded, or bulbous, or elongated, or doughnut or other tubular or non-tubular shape. The second chamber portion 26 has a shape configured for sealing against the external tissue of the stoma 22, and/or against the surrounding peristomal tissue 27. For example, the second chamber portion 26 may have a flared, or trumpet, or skirt or umbrella, tubular or non-tubular shape. The second chamber portion 26 has a larger extremity than the first chamber portion 24, such that the second chamber portion 26 extends further outwards radially than the first chamber portion 24.

The first and second chamber portions 24, 26 may be inflatable in common. For example, the first and second chamber portions 24, 26 may be interconnected by one or more communication channels, lumens or conduits, and a common inflation point may be used for inflating both chambers together. The pressure in the first and second chamber portions 24, 26 is balanced to thereby avoid high pressure concentration on only one side of the stoma 22. Depending on the desired design parameters, the communication channels may permit inflation fluid to move between the first and second chamber portions 24, 26 while the ostomy appliance 20 is being worn, to accommodate extreme body motion, and to maintain a balanced pressure in each chamber portion. Alternatively, the first and second chamber portions 24, 26 may be inflatable independently of each other. For example, the first and second chamber portions 24, 26 may be independent chambers, each with its own inflation point. This allows each chamber to be inflated to a different inflation pressure and/or prevent transfer of inflation fluid between chambers. A further alternative may be a hybrid of the above, using one or more communication channels or conduits between the first and second chamber portions 24, 26 to allow each chamber portion 24, 26 to be inflated from a common inflation point, but additionally including one or more inflation control valves. The valves can regulate the inflation pressure in each chamber portion 24, 26 and/or prevent deflation of each chamber portion 24, 26, to provide one or both chamber portions 24, 26 with a degree of independence.

Any suitable inflation means may be used to inflate the first and second chamber portions 24, 26. For example, a pump (such as a bellows pump) (not shown) may be integrated into the ostomy appliance 20. Alternatively, one or more inflation ports may be provided to allow an external pump (such as a syringe, an electric pump, or an oral inflation tube) to be connected. Any suitable inflation fluid may be used, for example, a gas (such as air), or a liquid (such as saline).

When the ostomy appliance 20 is to be removed, one or both of the inflation chamber portions 24, 26 is vented to discharge the inflation fluid. For example, the chamber portion(s) 24, 26 may be ruptured, or the inflation port opened, or a dedicated vent port opened. In one form, a tear-open seal may be torn open to vent the inflation fluid.

The ostomy appliance 20 may further comprise an adhesive wafer 34, having a skin-friendly adhesive for attachment to the skin. The adhesive wafer 34 may have an aperture 36 in which the seal is received. The aperture 36 may be roughly the same size as, or slightly larger than, the size of the second inflatable chamber portion 26. The aperture 36 is sufficiently large that it does not directly contact the stoma 22. The adhesive wafer 34 may support substantially the weight of the ostomy appliance 20 (and any ostomy device attached to the ostomy appliance 20) through the adhesive attachment to the skin, such that the seal itself is substantially independent of the weight.

In the first embodiment (FIG. 1), at least one of the inflation chamber portions 24, 26 completely occludes the stoma 22, in order to block the escape of body waste when inflated.

In the second embodiment (FIG. 2), the first and second chamber portions 24, 26 are a closed loop or "cuff" shape, for example, annular, doughnut, or tubular, with an aperture 36 for allowing body waste to be discharged via a communication or discharge passage 30 therethrough.

The second embodiment may optionally further comprise a support 28 for supporting the first and/or second chamber portions 24, 26. The support 28 may be of any suitable shape for supporting the first and second chamber portions 24, 26 in use. For example, the support 28 may include, or be formed as, a stem acting as a backbone for the first and second chamber portions 24, 26. The stem may pass generally centrally through the first and second chamber portions 24, 26. The stem may be at least partly deformable, for example, resilient, so as to avoid hard edges inside the stoma 22. The stem may be of a material that is generally stiffer than the flexible sealing walls of the first and second chamber portions 24, 26, or may inflate itself, becoming more structurally rigid upon inflation of the device, or may be constructed of the same material as the first and second chambers 24 and 26. The first and second chamber portions 24, 26 may meet, or be connected to or at the stem.

The stem may aid insertion of the first chamber portion 24, by providing a relatively self-supporting guide which can be inserted into the stoma 22, or another appliance may aid the insertion of the stem and first chamber portion 24. The stem may be tubular to define the communication passage 30 in the stoma 22. For example, the communication passage 30 may allow the discharge of body waste from the stoma 22, through the inflatable chamber portions 24, 26. In that case, the inflatable chamber portions 24, 26 serve to form an effective conformable and comfortable seal between the ostomy appliance 20 and the stoma 22, but not to contain body waste. An additional and/or external device (not shown), such as a collection pouch, or a removable plug or seal, is provided for managing the discharge of body waste through the communication passage 30. The support 28 may float somewhat with respect to the adhesive wafer 34 to allow the inflatable seal to self-locate within the stoma 22.

Figure 3:
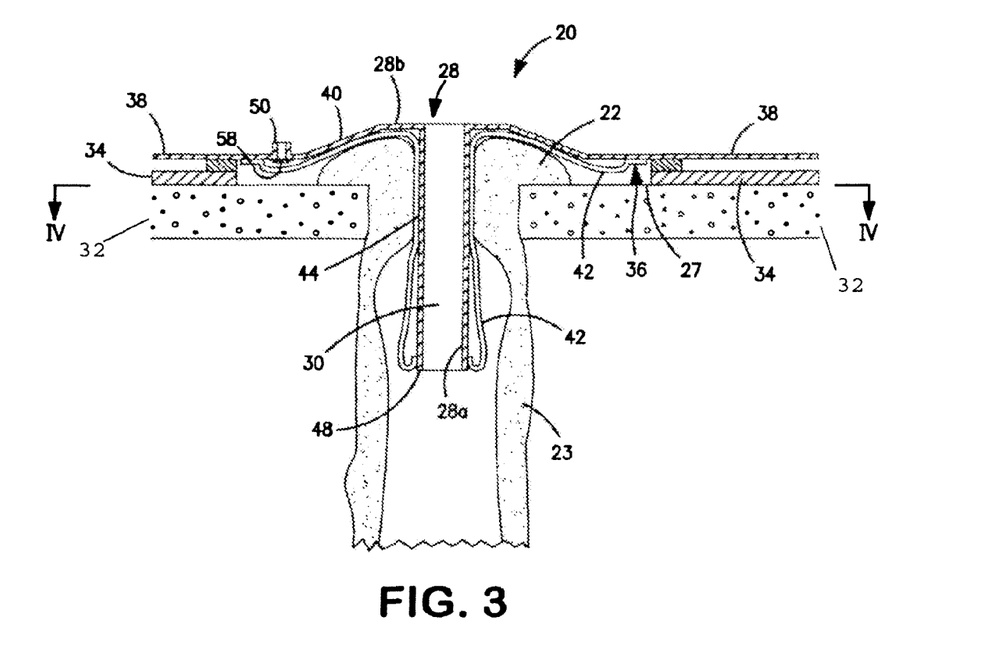
FIG. 3 is a schematic sectional view of a third embodiment of the invention, in the form of a stoma seal, in a deflated condition.
Figure 4:
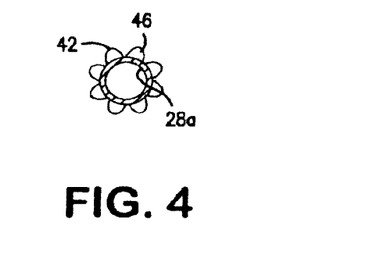
FIG. 4 is a schematic sectional view along the line IV-IV of FIG. 3 showing only the elements of the ostomy appliance.
Figure 5:
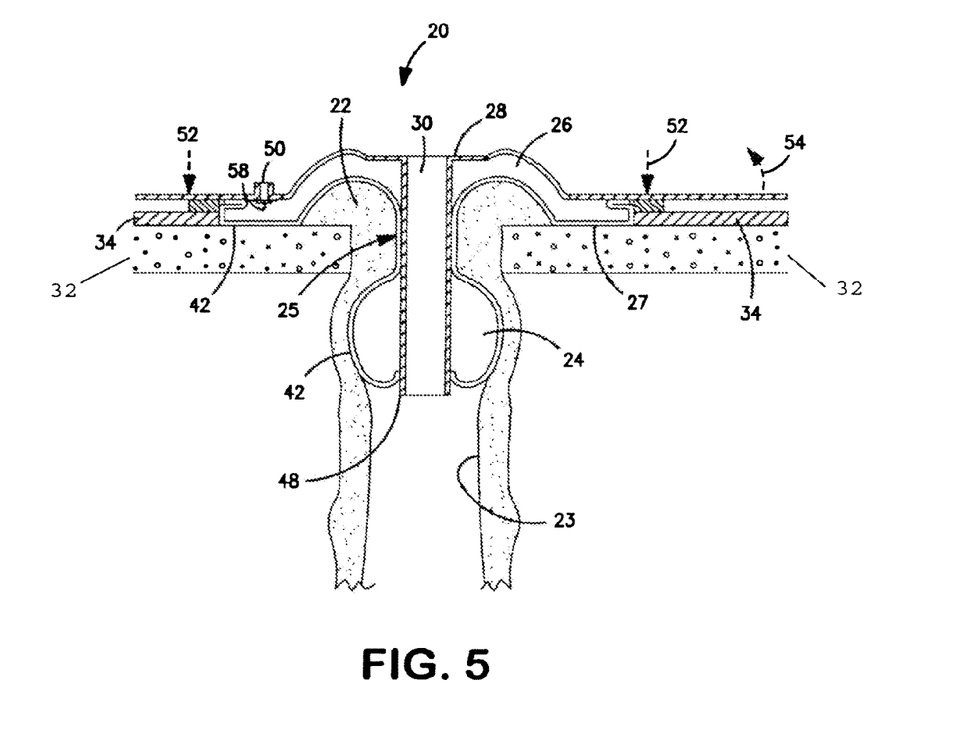
FIG. 5 is a schematic sectional view of the third embodiment in an inflated condition.

Referring to FIGS. 3-5, a third embodiment of the ostomy appliance 20 is described for sealing around a stoma opening 22 in a person's abdominal wall 32. The ostomy appliance 20 comprises an adhesive wafer 34 of a skin-friendly adhesive, and having an aperture 36 therein which is larger than the size of the stoma 22. By using a larger aperture, the adhesive does not adhere to the sensitive external tissue of the stoma 22 or the peristomal tissue 27, and the ostomate avoids associated pain in the sensitive external tissue of the stoma 22 or the peristomal tissue 27. A flange 38, for example, of plastics, is secured to the adhesive wafer 34, for example, by heat welding, or adhesive. The flange 38 supports a flexible annular rear wall 40 which in turn is coupled to a generally flat portion (base) 28b of a T-shape hollow support 28, or is coupled to the edge of a tubular-shaped hollow support 28 that has no flat portion 28b. The support 28 also includes a hollow stem 28a depending from the base 28b, or may comprise of the stem 28a itself. Also attached to the flange 38 is a flexible membrane 42. The flexible membrane 42 may be striated near a middle region 44 of the stem 28a, (e.g., attached to the stem 28a along a plurality of spaced, parallel axial bonds, to define a corrugated shape shown in FIG. 4, with parallel narrow connecting pathways 46 between the stem 28a and the flexible membrane 42). In FIG. 4, the size of the connecting pathways 46 are exaggerated, for the sake of schematic clarity. The connecting pathways 46 not only act as a fluidic connection between the first and second chambers 24, 26, but by varying the size and shape of the corrugations may also act as: (i) a cushion against the inner wall of the stoma 22; (ii) a friction reducer between the stem 28a and the inner wall of the stoma 22; (iii) flow restrictors between the first and second chambers 24, 26 by providing a damping effect to the volumetric changes between the chambers 24, 26; (iv) structurally inflatable columns that together act as the stem 28a, replacing it in the embodiment where the stem 28a is inflatable; (v) pathways for flatus to more easily escape between the corrugations and the inner wall of the stoma 22 in the embodiment where the stoma opening is normally closed and flatus escapes around the outside of the first and second chambers 24, 26. The flexible membrane 42 may further be attached to the stem 28a near its distal end 48.

The combination of the stem 28a (from the middle region 44 to the distal end 48) and the flexible membrane 42 (extending from the distal end 48 to the middle region 44 of the stem 28a) define the first inflatable chamber portion 24 (FIG. 5). The combination of the flange 38, the rear flexible or resilient wall 40, the base 28b, the stem 28a (down to the middle region 44), and the flexible membrane 42 defines the second inflatable chamber portion 26 (FIG. 5). The first and second chamber portions 24, 26 may communicate by means of the connecting pathways 46. The flexible or resilient rear wall 40 may be of thicker material than the flexible membrane 42 since the flexible membrane 42 may be desired to be more conformable to the shape of the stoma 22. Use of a thicker material for the flexible or resilient rear wall 40 can provide increased strength and protection against puncture in this externally facing wall. The flexible or resilient rear wall 40 may also be made of an elastic material or contain within it elastic material that once the device is inflated may be stretched to provide a gentle pressure and/or volumetric reserve which may assist with keeping the first and second chambers 24, 26 at a set pressure and/or provide an elastic rebound, and to more easily allow volumetric changes to occur between the chambers 24, 26 with embodiments where the chambers 24, 26 communicate. If the flexible or resilient rear wall 40 is made of an elastic material it may also enable the ostomy appliance 20 to accommodate very large stomas 22 by allowing a relatively high profile between the peristomal tissue 27 and the top of the stoma 22. The second chamber portion 26 may have a generally trumpet or umbrella type shape, when inflated, with a generally low profile externally facing surface. Bulging of the rear surface may be reduced by the presence of the base 28b of the support 28. This can provide a compact ostomy appliance 20, with a generally lower profile and more extensive fit than, for example, a simple doughnut shape, although the invention encompasses any shape of second chamber 26.

In use, the first and second chamber portions 24, 26 are initially deflated. The user presents the distal end portion 48 of the stem 28a to the stoma 22, and inserts the stem 28a until the adhesive wafer 34 presses against the skin (FIG. 3). Thereafter, the first and second chamber portions 24, 26 may be inflated (FIG. 5) by connecting an inflation source (not shown) to an inflation port 50 formed in the flange 38. The inflation port 50 may include a non-return valve 58, such as a flap valve, for preventing deflation through the inflation port 50. The inflation port 50 may communicate directly with the second inflatable chamber portion 26, and indirectly with the first inflatable chamber portion 24 via the connection pathways 46.

As can be seen in FIG. 5, the first and second chamber portions 24, 26 swell to form a conformable, large area seal against the external tissue of the stoma 22 and the peristomal tissue 27. This can achieve a reliable, conformable and comfortable seal and protect the peristomal tissue 27, without substantially restricting the mobility of the ostomate, and with less risk of the seal being affected by the wearer's movements. In the inflated condition, the support 28 floats somewhat with respect to the adhesive wafer 34, such that the waist 25 between the first and second chamber portions 24, 26 may self-locate at the stomal opening. Such floating and self-positioning further improves the seal performance, and reduce the effect of external forces on the seal.

In the embodiment shown, the ostomy appliance 20 does not necessarily include any device for managing the discharge of stool through the communication passage 30. The ostomy appliance 20 may, for example, be a mounting flange for a one-piece, or two-piece, ostomy device (not shown) such as a collection pouch or a controlled evacuation device. Such a device may be permanently or releasably attached to the flange 38, for example, at the position indicated at 52. With such a construction, the weight of, or the mounting force for supporting, the ostomy device may be borne substantially by the adhesive wafer 34. In the present embodiment, the principal function of the first and second inflatable chambers 24, 26 is to provide a seal around the stomal aperture 22, between the stomal aperture 22 and the ostomy appliance 20, rather than (i) providing a stoma occluding seal for blocking the discharge of stool from the stoma 22, or (ii) providing mechanical support for the ostomy device attached to the ostomy appliance 20. The ostomy appliance 20 may, for example, be a multi-use device, intended to remain in position at the stoma 22 for some time to provide a re-usable fixing point for one or more disposable devices such as disposable collection pouches. To this end, the ostomy appliance 20 may further comprise any of (not shown): a mechanical coupling profile; an adhesive bearing flange; and a landing flange for engagement by a complementary adhesive bearing flange on the ostomy device.

When it is desired to remove the ostomy appliance 20, the user deflates the first and second chamber portions 24, 26 in any of a number of different ways. For example, the user may puncture one or both of the first and second chamber portions 24, 26, or manipulate the inflation port 50 to vent the inflation fluid. Alternatively, the user may grip the flange 38 at the position 54, and tear the flange 38 itself, or separate the flange 38 from the adhesive wafer 34 to vent the second inflatable chamber portion 26 directly. The stem 28a is then withdrawn from the stoma 22, and the adhesive wafer 34 separated from the skin.

Figure 6:
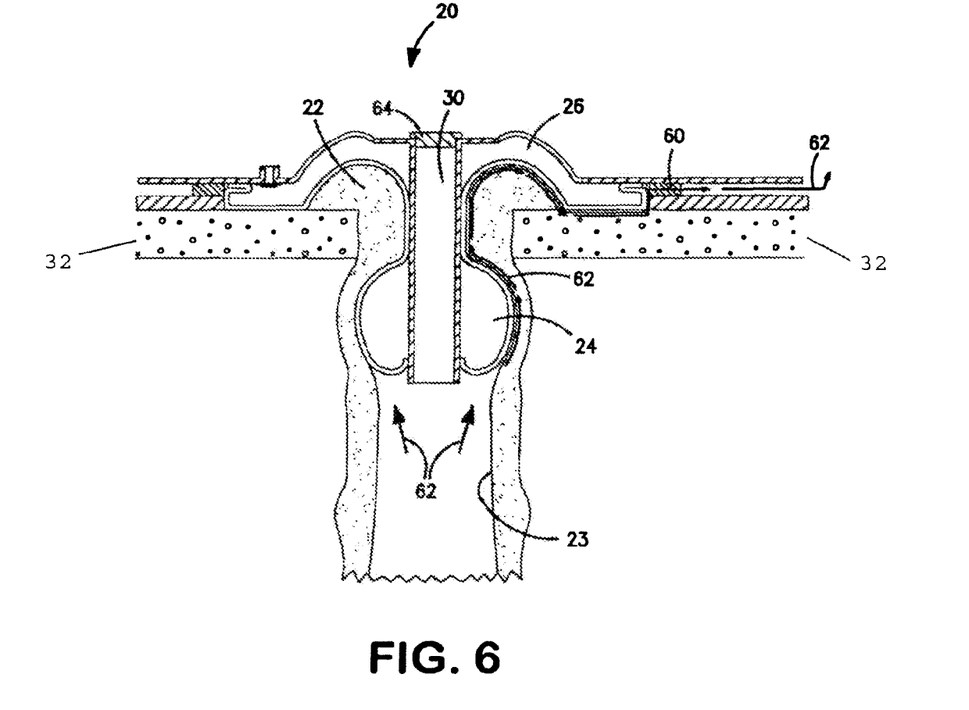
FIG. 6 is a schematic sectional view of a fourth embodiment that is a slight modification of the third embodiment.

Referring to FIG. 6, a fourth embodiment is illustrated similar to the third embodiment, except that a deodorizing filter 60 is provided for deodorizing vented flatus. This is especially, but not exclusively, useful where the stoma opening is normally closed (e.g., by a closure seal 64) and flatus escapes around the outside of the first and second chambers 24, 26 and through the filter 60 as shown by arrows 62 in FIG. 6. This filter 60 or an exhaust passageway may be present in the other embodiments to allow air to escape from the ostomy appliance 20 during inflation.

Figure 7:
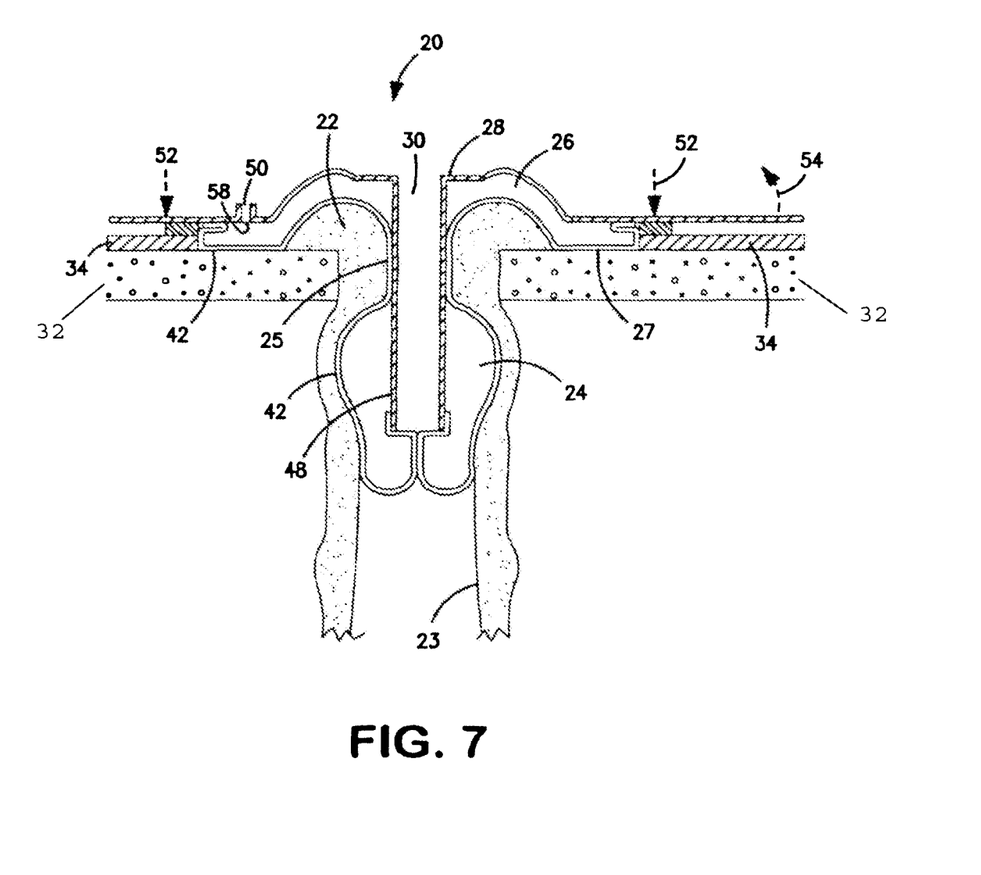
FIG. 7 is a schematic sectional view of a fifth embodiment that is a further slight modification of the third embodiment.
Figure 8:
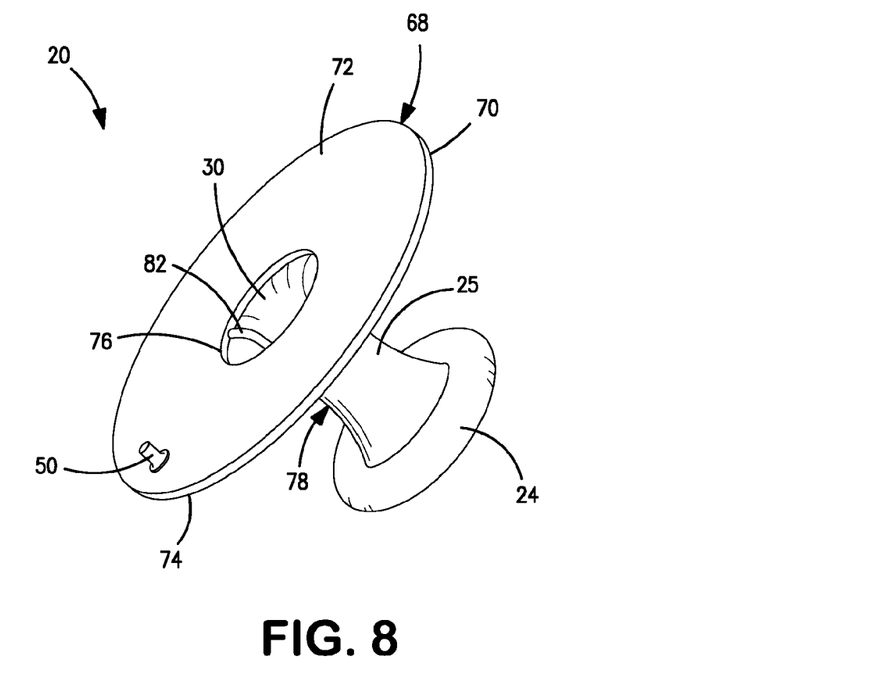
FIG. 8 is a schematic front perspective view of a sixth embodiment in an inflated condition.
Figure 9:
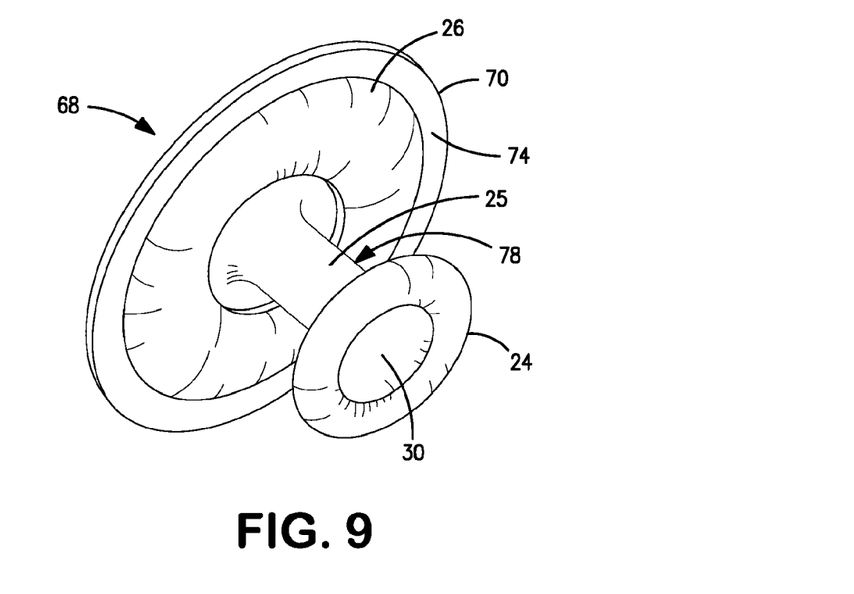
FIG. 9 is a schematic rear perspective view of the sixth embodiment.

Referring to FIG. 7, a fifth embodiment is illustrated similar to the third embodiment. The main difference is that the flexible membrane 42 has sufficient material within the rectal chamber so, when inflated, the first chamber 24 forms a closure in front of the distal end 48 of the stem 28a as shown in FIG. 7. This closure may be opened to discharge waste by partially deflating and/or reducing the pressure within the ostomy appliance 20 but retain enough to maintain the ostomy appliance 20 in place. This embodiment may also be combined with the exhaust passageway with or without the deodorizing filter of FIG. 6.

Referring to FIGS. 8-11, a sixth embodiment of ostomy appliance 20 comprises an integral component 68 comprising a faceplate 70 having a front surface 72 and a rear surface 74, and an aperture 76 for passing stomal waste; a stem 78 projecting rearwardly from around the aperture 76; a first inflatable chamber 24 disposed near or at the distal end of the stem 78, and a second inflatable chamber 26 disposed on the rear surface 74. The faceplate 70 is optionally relatively rigid compared to one or more of the other materials defining the chambers 24 and 26 and the stem 78, to provide a support for at least the second chamber 26, and/or to reduce the external profile height of the component when in use. The stem 78 can be hollow and communicate with the aperture 76 of the faceplate, to provide a discharge passage for stomal waste without having to remove the component 68 from the stoma 22.

In the illustrated embodiment, the integral component 68 is made from two pieces, namely the faceplate 70, and a second piece 80 (FIGS. 10 and 11) attached to the faceplate 70. The faceplate 70 is, in this example, substantially planar and may be cut or stamped from flat stock. The second piece 80 is optionally molded from plastics material that is more flexible than the faceplate 70. The second piece 80 includes an annular shell portion 80a that, together with the faceplate 70 defines the second chamber 26. The shell portion 80a is attached to the faceplate 70 at positions 81a and 81b to define the chamber 26. The attachment may be any form of welding or bonding. The second piece 80 further includes the stem 78 and the first chamber 24. A first end of the stem 78 adjacent to the first chamber 24 is flared. A second end of the stem 78 adjacent to the faceplate 70 may also be flared; the degree of flaring at the second end may be smaller than at the first end. In the present embodiment, the second piece 80 is resiliently flexible. The tubular and/or flared shape of the stem 78 provides gentle elastic support for the first chamber 24 with respect to the faceplate 70. The elastic rebound of the stem 78 generally prevents the first chamber 24 from turning within the bowel, and maintains the first chamber against the bowel wall with gentle elastic force. In the present form, the stem 78 is not itself inflatable, but the stem 78 could be wholly or partly inflatable as in the preceding embodiments, if desired. The stem 78 may be resiliently expandable upon passage of bulk stomal waste therethrough.

The first and second chambers 24, 26 communicate via a lumen or conduit 82, and are inflatable via a common inflation point 50 formed, for example, on the faceplate 70. The conduit 82 may be integral with the stem 78, or it may be separate tube that passes through the wall material to communicate with the first and second chambers 24, 26. Alternatively, the first and second chambers 24, 26 may be inflatable independently of each other. In such case, as illustrated in phantom in FIG. 10, the conduit 82 may extend from the first chamber 24 to a second inflation port 84 instead of coupling the first and second chambers 24, 26 together.

Figure 10:
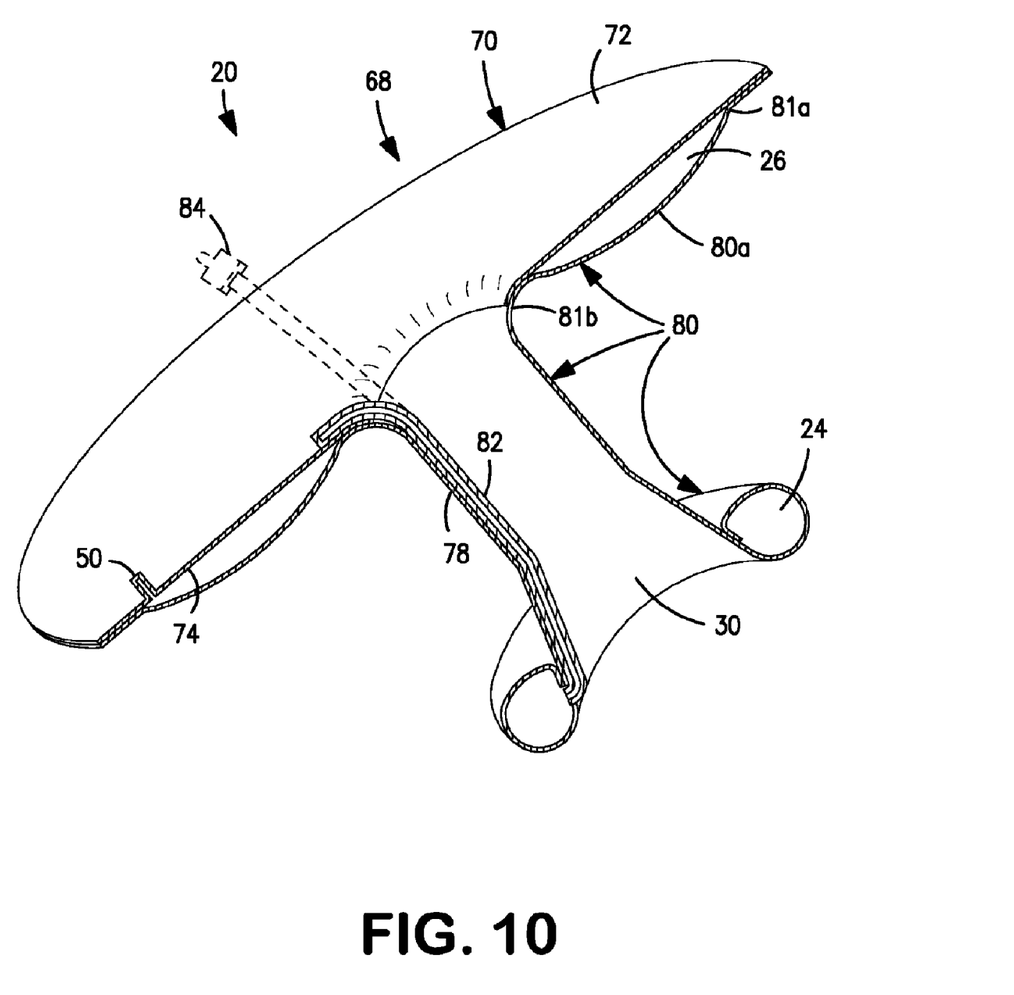
FIG. 10 is an enlarged cut-through perspective view of the sixth embodiment, similar to FIG. 8.
Figure 11:
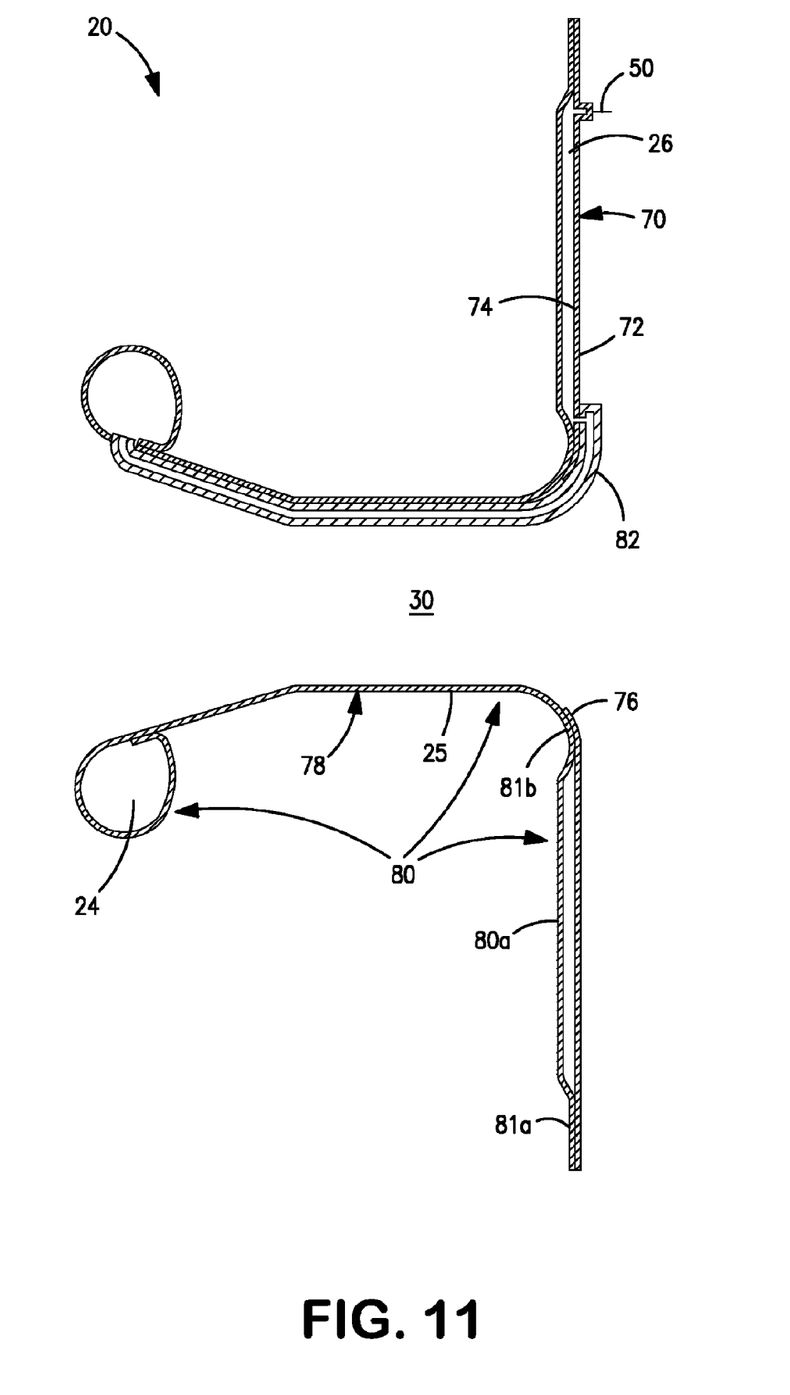
FIG. 11 is a schematic sectional view through the sixth embodiment.

The material characteristics for the faceplate 70 and the second piece 80 may be chosen to provide the desired strengths and elasticity for each component. In one form, the faceplate 70 and the second piece 80 are made from the same material and same material thickness (in a case where the faceplate 70 is not substantially more rigid than the second piece 80). In another form, the faceplate 70 is made of the same material as the second piece 80, but with a different durometer and/or thickness. In another form, the faceplate 70 is substantially rigid.

A preferred material for the second piece 80 is silicone rubber. Example characteristics include approximately 0.012 inches thick and/or approximately 35 shore A durometer. Such material may be injection molded and is reasonably elastic. An alternative material is urethane film. An example thickness is approximately 0.012 inches thick. Such a material may be dip molded, and is less elastic than the silicone rubber example.

A preferred material for the faceplate 70 is silicone rubber. Example characteristics include (i) approximately 0.012 inches thick and/or approximately 80 shore A durometer; (ii) approximately 0.25 inches thick and/or approximately 35 shore A durometer. An alternative material is polycarbonate, for example, with a thickness of approximately 0.062 inches.

Similar materials may also be used for the other embodiments.

In a slightly modified form, the annular shell portion 80a is made from a different piece of material from the stem 78 and the first chamber 24. In other words, the component 68 comprises three pieces joined together, namely: the faceplate 70, the annular shell portion 80a, and a third piece defining the stem 78 and the first chamber 24. The annular shell portion 80a can be made of the same material as the third piece, such as silicone rubber or urethane film. If desired, the material thickness and/or durometer may be varied to give different characteristics between the first and second chambers 24 and 26.

In use, the integral component 68 may find different uses as a stoma seal usable in a controlled evacuation stoma port. If desired, a secondary seal may be made by an additional component against the front face 72 of the faceplate 70. The component 68 may also find use as a comfortable seal and/or stoma extender for a non-continent ostomy appliance, such as a collection pouch. The collection pouch may form a direct or indirect fit against the faceplate, for example, using an adhesive coupling.

The faceplate 70 may be received in an aperture of an adhesive pad or other ostomy appliance component, in a similar manner to the preceding embodiments. Such attachment can anchor or restrain movement of the component 68. In one form, the faceplate 70 is attachable to another ostomy appliance component by a snap-fit.

Modifications may be made to these preferred embodiments and still remain within the scope of the claimed invention.

I claim:

1. An ostomy appliance comprising an inflatable seal for forming a seal at a stoma, the inflatable seal comprising:
    a first inflatable chamber portion for insertion into the stoma for forming an internal seal;
    a second inflatable chamber portion for forming an external seal with respect to the stoma; and
    a plurality of corrugated inflatable columns intermediate the first and second inflatable chamber portion defining passageways for inflation fluid and pathways for escape of flatus.

2. The ostomy appliance according to claim 1, wherein the second chamber portion is configured to form an external seal against at least one of: the external stoma tissue; and peristomal skin.

3. The ostomy appliance according to claim 1, further comprising a waist defined between the first and second chamber portions, the waist defining a portion narrower than both the first and second chamber portions, the waist is configured, in use, to seat at the narrowest part of the stoma.

4. The ostomy appliance according to claim 1, wherein the first and second chamber portions are cuff-shaped, the appliance further comprising a discharge passage extending through the first and second chamber portions.

5. The ostomy appliance according to claim 4, wherein the discharge passage is defined at least partly by a support coupled to at least one of the first and second chamber portions and having a stiffness greater than the first and second chamber portions.

6. The ostomy appliance according to claim 5, wherein the first and second chamber portions are mutually coupled at the support.

7. The ostomy appliance according to claim 5 wherein the first and second chamber portions are defined at least partly by a membrane that is sealed to the support at one or more positions.

8. The ostomy appliance according to claim 7, wherein the first inflatable chamber has sufficient material so when inflated the internal inflatable chamber forms a closure in front of a distal end of the support.

9. The ostomy appliance according to claim 8, wherein the closure is opened to discharge waste by partially deflating and/or reducing the pressure within the device but retains enough pressure to maintain the device in place, then reclosed.

10. The ostomy appliance according to claim 5, wherein the support has a shape selected from: generally tubular; generally hollow T-shape;
    generally planar with an aperture.

11. The ostomy appliance according to claim 4, wherein the discharge passage is defined at least partly by an inflatable support coupled to at least one of the first and second chamber portions, the inflatable support is defined as by at least one of the inflatable columns.

12. The ostomy appliance according to claim 1, wherein the first and second chamber portions are inflatable in common.

13. The ostomy appliance according to claim 12, wherein there is an elastic portion of at least one of the first and second chamber portions where the extension of the elastic portion allows volumetric changes to occur between the chambers.

14. The ostomy appliance according to claim 1, wherein at least one of the first and second chamber portions has a respective inflated shape selected from one or more of: rounded; cuff; bulbous; doughnut; flared; trumpet; skirt; and umbrella.

15. The ostomy appliance according to claim 1, wherein one of the chamber portions is larger in maximum diameter than the other.

16. The ostomy appliance according to claim 1, further comprising an adhesive member carrying a skin-friendly adhesive, the adhesive member having an aperture in which the inflatable seal is located.

17. The ostomy appliance according to claim 16, wherein the inflatable seal is configured, in use, to fill the free area of the aperture in the adhesive member.

18. The ostomy appliance according to claim 16, further comprising a mounting portion for mounting a body waste collecting or managing device, the mounting portion being supported by the adhesive member.

19. An ostomy appliance including a stoma extender for intimate engagement with a stoma, the stoma extender comprising:
   a tubular discharge channel having a first end for insertion into a stoma for providing a discharge path from the first end within the stoma to a second end externally of the stoma;
   a first inflatable chamber portion coupled to the discharge channel and configured for insertion into the stoma for diverting effluent into the discharge channel of the stoma extender;
   a second inflatable chamber portion for fitting against tissue externally of the stoma; and
   a plurality of corrugated inflatable columns intermediate the first and second inflatable chamber portion defining passageways for inflation fluid and pathways for escape of flatus.

20. The ostomy appliance of claim 19, wherein in use the second end of the discharge channel projects above the stoma, whereby the stoma extender extends the discharge path compared to the stoma alone.

21. The ostomy appliance of claim 19, further comprising a tubular stem defining at least partly the discharge channel, the tubular stem including a flared shape at at least one end.

* * * * *